US010646136B2

(12) United States Patent
Cummings

(10) Patent No.: US 10,646,136 B2
(45) Date of Patent: May 12, 2020

(54) KNEE GONIOMETER TO MEASURE KNEE EXTENSION DIFFERENCE AND EXTENSOR LENGTH

(71) Applicant: Kevin G. Cummings, Essex Junction, VT (US)

(72) Inventor: Kevin G. Cummings, Essex Junction, VT (US)

( * ) Notice: Subject to any disclaimer, the term of this patent is extended or adjusted under 35 U.S.C. 154(b) by 0 days.

(21) Appl. No.: 16/033,039

(22) Filed: Jul. 11, 2018

(65) Prior Publication Data
US 2020/0015710 A1   Jan. 16, 2020

(51) Int. Cl.
*A61B 5/107* (2006.01)
*A61B 5/00* (2006.01)
*A61B 5/11* (2006.01)
*G01B 5/24* (2006.01)

(52) U.S. Cl.
CPC .......... *A61B 5/1071* (2013.01); *A61B 5/4528* (2013.01); *A61B 5/4585* (2013.01); *A61B 5/1121* (2013.01); *G01B 5/24* (2013.01)

(58) Field of Classification Search
CPC .......... A61B 5/1071; A61B 5/107; B43L 7/10
USPC ......................................... 33/512, 473, 515
See application file for complete search history.

(56) References Cited

U.S. PATENT DOCUMENTS

| | | | |
|---|---|---|---|
| 1,040,284 A * | 10/1912 | Cunningham | B43L 7/12 33/473 |
| 1,863,236 A * | 6/1932 | Brienza | A41H 1/02 33/7 |
| 3,273,246 A | 9/1966 | Siberini | |
| 4,436,099 A | 3/1984 | Raftopoulos | |
| 4,834,057 A | 5/1989 | McLeod, Jr. | |
| 4,872,268 A * | 10/1989 | Perrault | A61B 5/103 33/512 |
| 5,263,492 A | 11/1993 | Voyce | |
| 5,461,794 A | 10/1995 | Huang | |
| 6,049,990 A | 4/2000 | Holland | |
| 6,834,437 B1 * | 12/2004 | Kilgore | A61B 5/1074 33/3 B |
| 7,082,692 B2 | 8/2006 | Shapiro | |
| 7,739,806 B1 | 6/2010 | Pater | |
| 7,942,799 B1 | 5/2011 | Boyd | |
| 8,341,850 B2 | 1/2013 | Merchant | |
| 8,567,081 B2 * | 10/2013 | Smith | A61B 5/0082 33/515 |

(Continued)

*Primary Examiner* — Christopher W Fulton
(74) *Attorney, Agent, or Firm* — New York Law School PPC

(57) ABSTRACT

A device and method for measuring the amount of knee extension loss, hyperextension, or extensor length associated with arthritis, trauma, surgery or other medical conditions. This device and method includes measuring the difference in heel heights of a patient while patient is lying prone on a table with their legs, at the level of their knee caps, off the table. This device and method also measures extensor length in a patient's knee joint, by assessing heel height difference while a patient is lying prone on a table with a prone knee bend. This device and its methods provide accurate distance measurements that correlate to knee straightness and flexibility; these distinguishing metrics are unattainable by a standard "disc" goniometer. In addition, this device permits convenient measuring of a knee's mobility for two unique perspectives, namely in prone with legs straight or with a knee bent.

15 Claims, 9 Drawing Sheets

(56) References Cited

U.S. PATENT DOCUMENTS

| | | | |
|---|---|---|---|
| 2003/0149378 A1* | 8/2003 | Peabody | A61B 5/1072 600/587 |
| 2006/0090360 A1 | 5/2006 | Shapiro | |
| 2006/0168835 A1* | 8/2006 | Casner | B25H 7/00 33/473 |
| 2006/0174504 A1* | 8/2006 | Szumer | B25H 7/02 33/613 |
| 2007/0266579 A1 | 11/2007 | Briscoe et al. | |
| 2013/0303947 A1* | 11/2013 | Gamet | A61B 5/0488 600/595 |
| 2015/0201866 A1* | 7/2015 | Wojcieszak | A43D 1/02 33/512 |
| 2016/0000369 A1* | 1/2016 | Minnifield | A61B 5/1072 600/595 |

* cited by examiner

The method- 120

KNEE GONIOMETER TO MEASURE KNEE EXTENSION DIFFERENCE AND EXTENSOR LENGTH

BACKGROUND INFORMATION

A knee goniometer device is a bio-medical measuring device used in the rehabilitation setting to measure an anatomic angle of the knee. The knee goniometer may be used by orthopedic surgeons, physician assistants, and especially clinicians such as physical therapists, athletic trainers, and physical therapy assistants, etc. The knee goniometer device is used by a practitioner to measure the lack of knee extension, commonly known as straightness. In some instances, it may be used to assess hyperextension, also known as excessive straightness. Also, it may assess knee extensor length, often referred to as "quadriceps flexibility".

Knee extension, hyperextension, and knee extensor length may become a problem with arthritis, injury, or after surgery. Patients who have experienced major knee trauma, with or without a later surgery, may have motion loss or hypermobility. A lack of extension may be called a "knee flexion contracture" because the knee motion is restricted in a small amount of flexion (bend). The average knee range of motion is 0 to about 135 degrees; some research reports 140 degrees. Often, a person may have an amount of hyperextension (straightness beyond zero) because of a person's anatomy structure or by injury. Hyperextension is sometimes noted in medical charts as a positive. For example, the person would have +5 to 135 degrees range of motion. On a standard "disc" goniometer (indicia are in degrees), 0 degrees indicates full (normal) extension, whereas 5 degrees hyperextension is within normal limits. Knee extensor length indicates a person's quadriceps muscle tightness.

A standard "disc" goniometer provides an angle reference measurement read by a user while the "disc" goniometer is held alongside a patient's knee. The "disc" goniometer requires a user to align one reference arm with the patient's upper leg, and a second reference arm with the patient's lower leg. The precision of the angle measurement relies on user expertise and perspective because the "disc" goniometer does not positively engage any part of a patient's leg. Measurements may vary based on a change of user or change in "disc" goniometer model type.

After surgery, it is important to regain normal motion as soon as possible in most protocol cases. Although, in a posterior cruciate ligament (PCL) reconstruction, rehabilitation is different as hyperextension is not desired. Ideally, restoring full knee extension properly allows for normal walking, improved function, and less pain. During post-surgical physical therapy, doctors commonly emphasize to patients that extension needs to be worked on more than flexion, because the connective tissue properties of the knee allows flexion to advance easier. Usually the goal is to attain the same amount of extension and knee extensor length in the surgically repaired knee as non-injured knee.

Documenting the amount of extension or knee extensor length helps with insurance coverage, indication of progress, and patient motivation. The knee goniometer may also be used for orthopedic research.

SUMMARY

In the first exemplary embodiment, the knee goniometer device is disclosed that provides assessment of knee joint extension or hyperextension by measuring heel height difference of a patient while positioned lying prone on a table with their legs, at the level of their knee caps, off the table.

In the second exemplary embodiment, a method is disclosed of using the knee goniometer device to measure extension loss and/or hyperextension in a patient's knee joint, by assessing heel height difference while a patient is lying prone on a table with their legs, at the level of their kneecaps, off the table.

In the third exemplary embodiment, a method is disclosed of using the knee goniometer device to measure extensor length in a patient's knee joint, by assessing heel height difference while a patient is placed in a flat, face down position during a knee bend.

DETAILED DESCRIPTION

Figure 1:
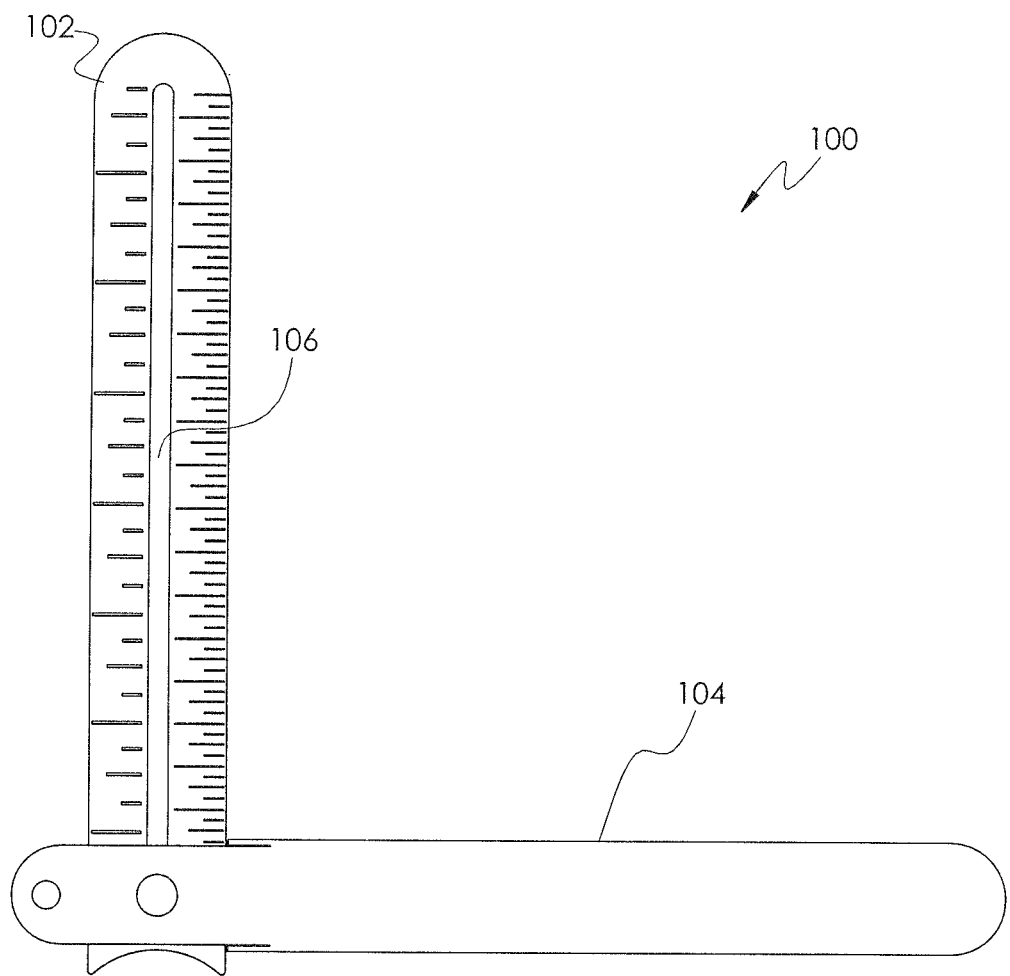
FIG. 1 shows an anterior view of the knee goniometer device in its deployed state at zero extension according to an exemplary embodiment.

The exemplary embodiments may be further understood with reference to the following description and the related appended drawings, wherein like elements are provided with the same reference numerals. The exemplary embodiments are related to a device and method for accurately assessing the difference in extension or hyperextension between the patient's knees by measuring a heel height difference of a patient while the patient is lying prone on a table with their legs, at the level of their knee caps, off the table.

FIG. 1 shows an anterior view of the exemplary knee goniometer device in its deployed at zero extension. The knee goniometer device 100 comprises an elongated ruler member 102 and an elongated movable member 104. The elongated ruler member 102 and the elongated movable member 104 may be construed of a rigid or a semi-rigid material such as wood, plastic, composite material, etc. The elongated ruler member 102 has a longitudinal slot 106 that allows the elongated movable member 104 to move in relation to the elongated ruler member 102.

Figures 2, 3:
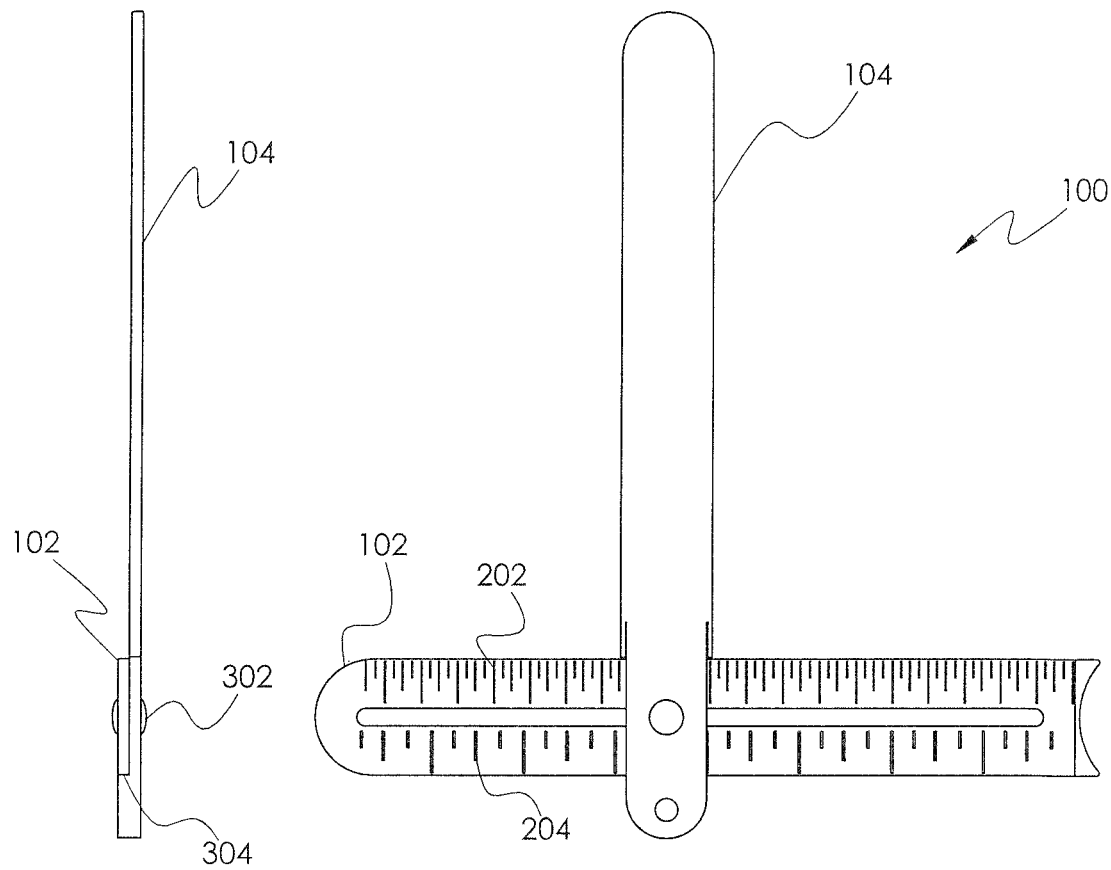
FIG. 2 shows an anterior view of the knee goniometer device in its deployed and half-extended state according to an exemplary embodiment.
FIG. 3 shows a bottom view of the knee goniometer device in its deployed state according to an exemplary embodiment.

FIG. 2 shows an anterior view of the knee goniometer device 100 in its deployed and partially-extended state. This view shows that the calibrated indicia 202 and 204 are located on at least one surface of a front side of the elongated ruler member 102. In this example, the calibrated indicia 202 and 204 are located on opposite sides of the surface of the elongated ruler member 102.

FIG. 3 shows a bottom view of the knee goniometer device 100 in its deployed state. The elongated movable member 104 is attached to the elongated ruler member 102 with a fastener 302. A flange 304 of the elongated movable member 104 allows the elongated movable member 104 and the elongated ruler member 102 to engage in a perpendicular orientation. As described above, in the deployed state, the elongated moveable member 104 and the elongated ruler member 102 are oriented perpendicular to each other. The flange 304 of the elongated moveable member 104 allows a flat side of the elongated ruler member 102 to sit on the flange 304 to assure this perpendicular orientation. The flange 304 is substantially the same width as the elongated ruler member 102.

Figure 4:
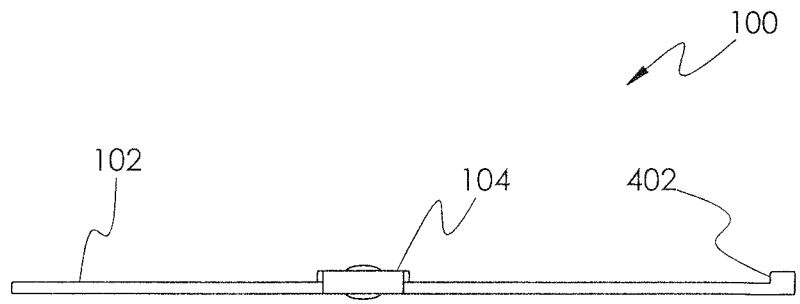
FIG. 4 shows a side view of the knee goniometer device in its deployed and half-extended state according to an exemplary embodiment.

FIG. 4 shows the side view of the knee goniometer device 100 in a deployed and partially-extended position. A shelf 402 provides a perpendicular planar surface for the elongated movable member 104 to sit on the elongated ruler member 102 at a measurement of zero heel height difference. For example, FIG. 1 shows the knee goniometer device 100 in the zero heel height difference. The shelf 402 stops the elongated moveable member 104 from moving past this zero position.

Figure 5:
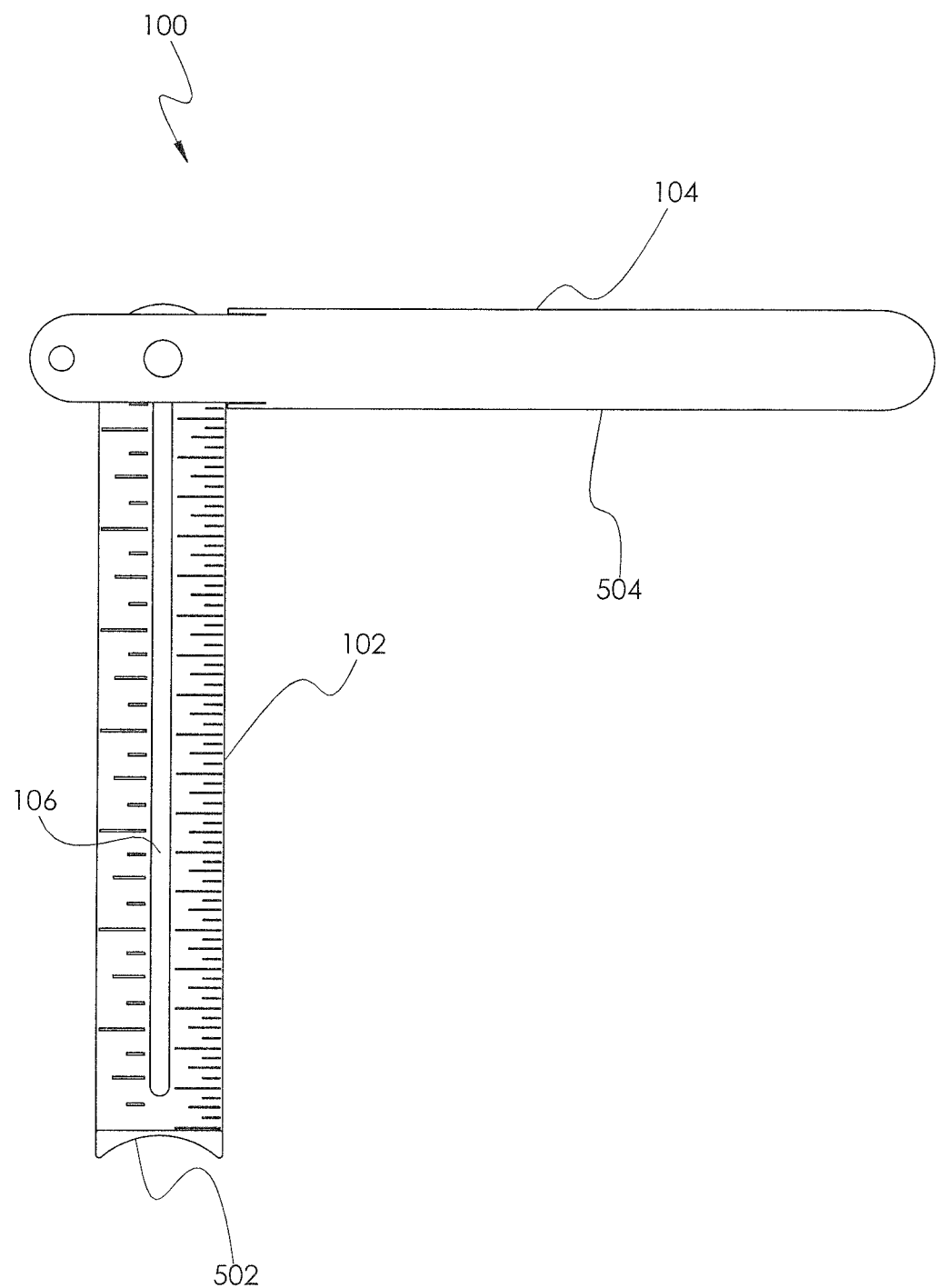
FIG. 5 shows an anterior view of the knee goniometer device in its deployed and fully extended state according to an exemplary embodiment.

FIG. 5 shows the anterior view of the knee goniometer device 100 in an open and fully deployed position. The elongated ruler member 102 has at one end a concave fossa 502 to receive a heel. When the knee goniometer device 100 is in use, the concave fossa 502 rests on the posterior aspect of the visually lower heel of the patient's leg while patient is lying prone, face down, on a table with their legs, at the level of their knee caps, off the table. Thus, the elongated ruler member 102 is positioned vertically on the heel of the patient's leg. The elongated movable member 104 is slidably attached to the elongated ruler member 102 and may slide along the longitudinal slot 106 located in the elongated ruler member 102 until surface 504 of the elongated movable member 104 contacts the visually higher heel of the patient's leg. As described above, when being used for taking a measurement, the elongated movable member 104 is positioned substantially perpendicular to the elongated ruler member 102.

Figure 6A:
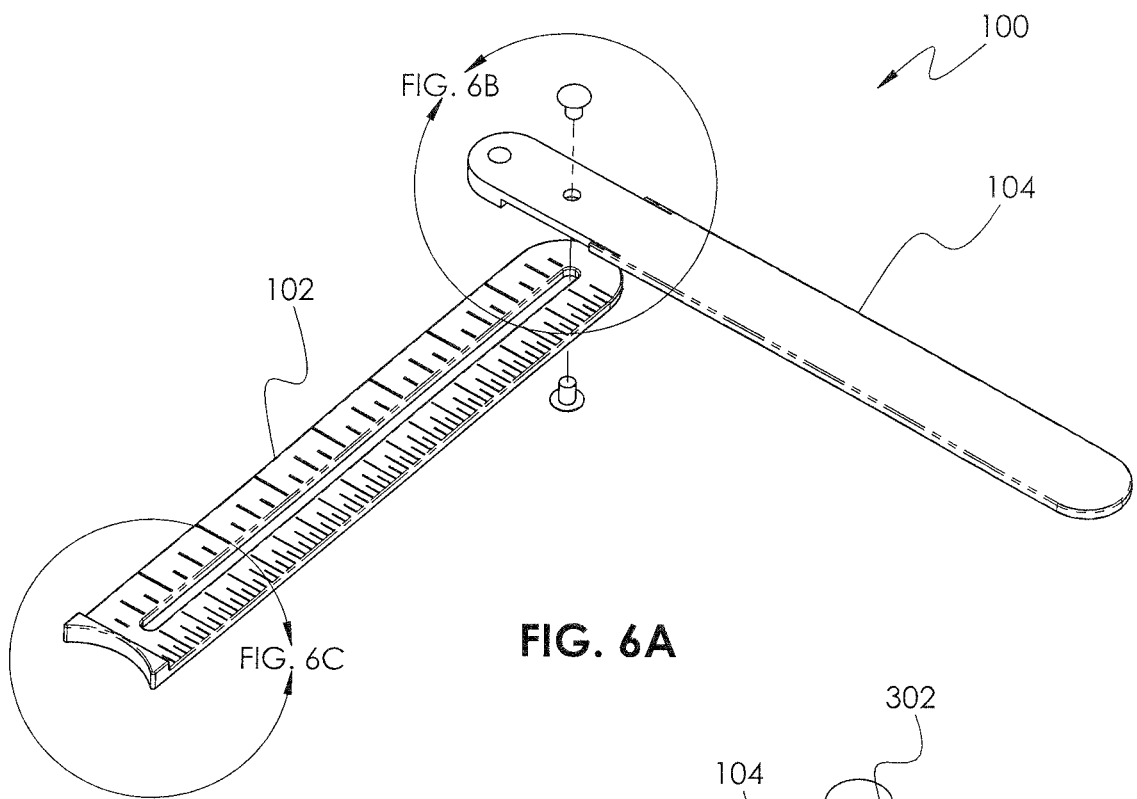
FIGS. 6A, 6B, and 6C show anterior exploded and magnified views of the knee goniometer device in its deployed and fully extended state according to an exemplary embodiment.

FIG. 6A shows an exploded perspective view of the anterior side of the knee goniometer device 100 in its deployed and fully extended state.

Figure 6C:
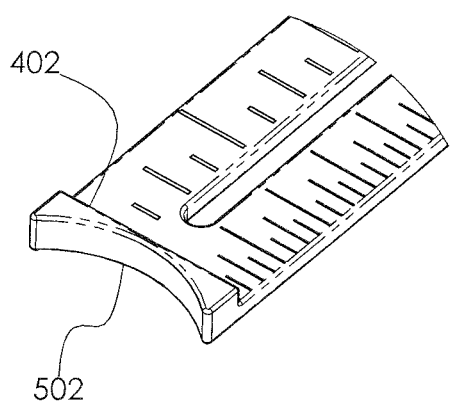
Figure 6B:
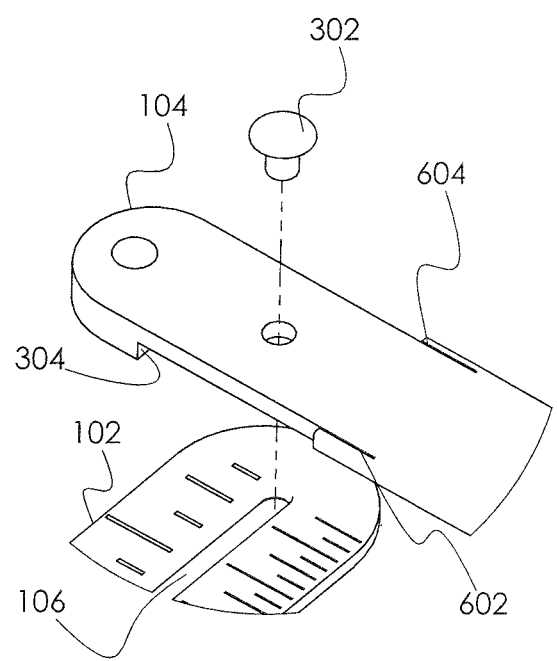

FIG. 6B shows the elongated movable member 104 having bilateral reference lines 602 and 604. The bilateral reference lines 602 and 604 allow the user to read the adjacent calibrated indicia of the elongated ruler member 102 wherein the measurement is then recorded by the user. The bilateral reference lines 602 and 604 on the elongated movable member 104 permit measurement of heel height difference on either the left side or right side of the elongated ruler member 102. When measuring the patient's right leg, patient heel height difference is read from the reference line at position 602. When measuring the patient's left leg, the elongated movable member 104 pivots to the left side of the elongated ruler member 102, and patient heel height difference is read from the reference line at position 604. It should be clear to one skilled in the art that while the elongated moveable member 104 and the elongated ruler member 102 are positioned perpendicularly in the deployed state, the elongated moveable member 104 may extend perpendicularly with respect to either side of the elongated ruler member 102 depending on which leg is to be measured.

FIG. 6B further shows the anterior view of the elongated movable member 104 being attached to the elongated ruler member 102 by the fastener 302. The fastener 302 penetrates the top of the elongated movable member 104 and proceeds through the longitudinal slot 106 on elongated ruler member 102 which allows elongated ruler member 102 to attach to the flange 304 of the elongated movable member 104. This allows the elongated movable member 104 and elongated ruler member 102 to engage in perpendicular orientation. It should also be clear that the fastener 302 is fastened in such a manner that it is freely moveable within the longitudinal slot 106 allowing the elongated moveable member 104 to move with respect to the elongated ruler member 102.

FIG. 6C shows another anterior view of the end of the elongated ruler member 102 and the concave fossa 502. The shelf 402 provides a surface for the elongated movable member 104 to sit on the elongated ruler member 102 at a measurement of zero heel height difference. If a patient has zero difference in heel height, the elongated movable member 104 will contact the shelf 402 and provide a zero measurement at either position 602 or position 604.

Figure 7A:
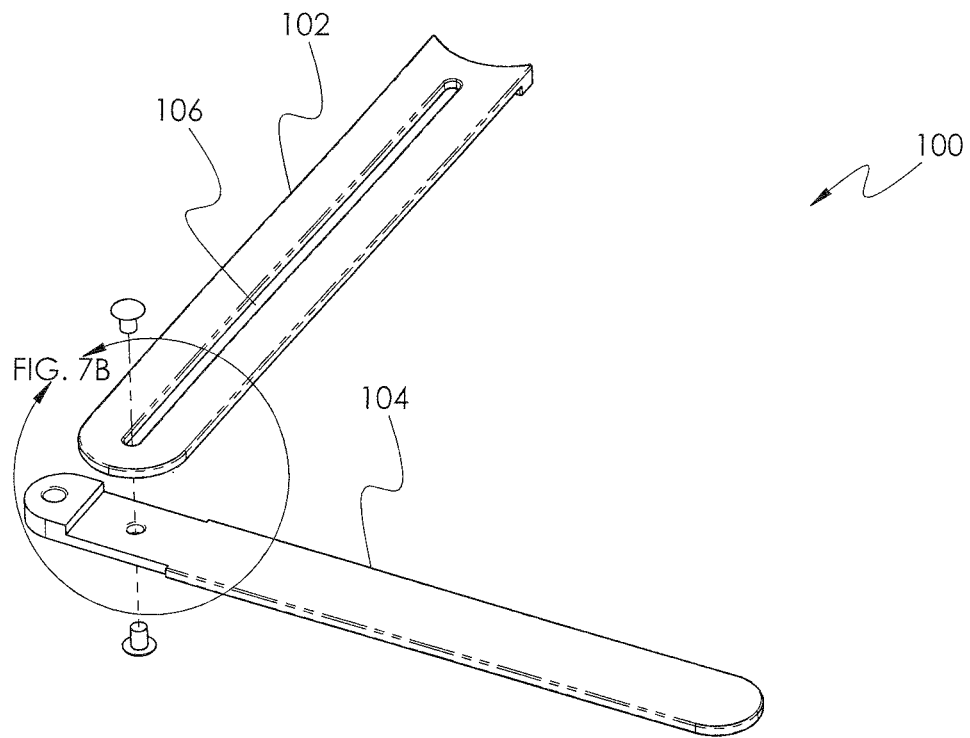
FIGS. 7A and 7B show posterior exploded and magnified views of the knee goniometer device in its deployed and fully extended state according to an exemplary embodiment.

FIG. 7A shows an exploded perspective view of the posterior side of the knee goniometer device 100 in its deployed and fully extended state. It is noted that the calibrated indicia 202 and 204 may also be provided on other surfaces. For example, the outward facing surface of the elongated ruler member 102 may also include calibrated indicia.

Figure 7B:
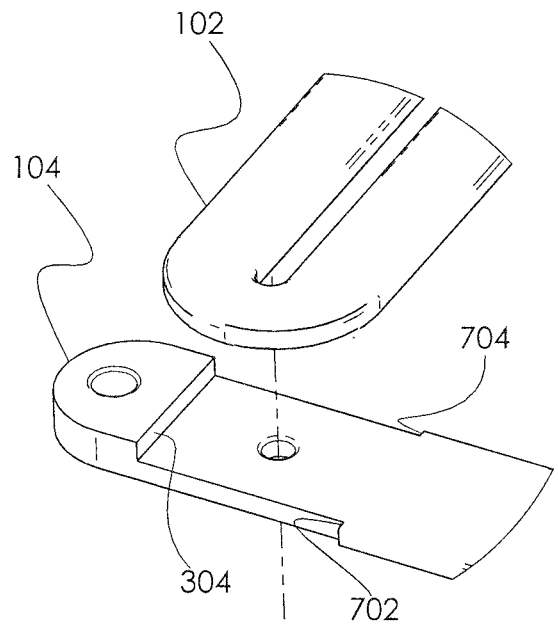

FIG. 7B shows a posterior view of the knee goniometer device 100. The elongated movable member 104 having transversely opposed notches 702 and 704 at one end that narrow the width of the elongated movable member 104. The depth of the notches 702 and 704 are each substantially the same as the width of the surface of the shelf 402 to the apex of the concave fossa 502. In zero heel height difference, this allows for accurate horizontal accordance of the apex of the concave fossa 502 with surface 504 of the elongated movable member 104.

Figure 8:
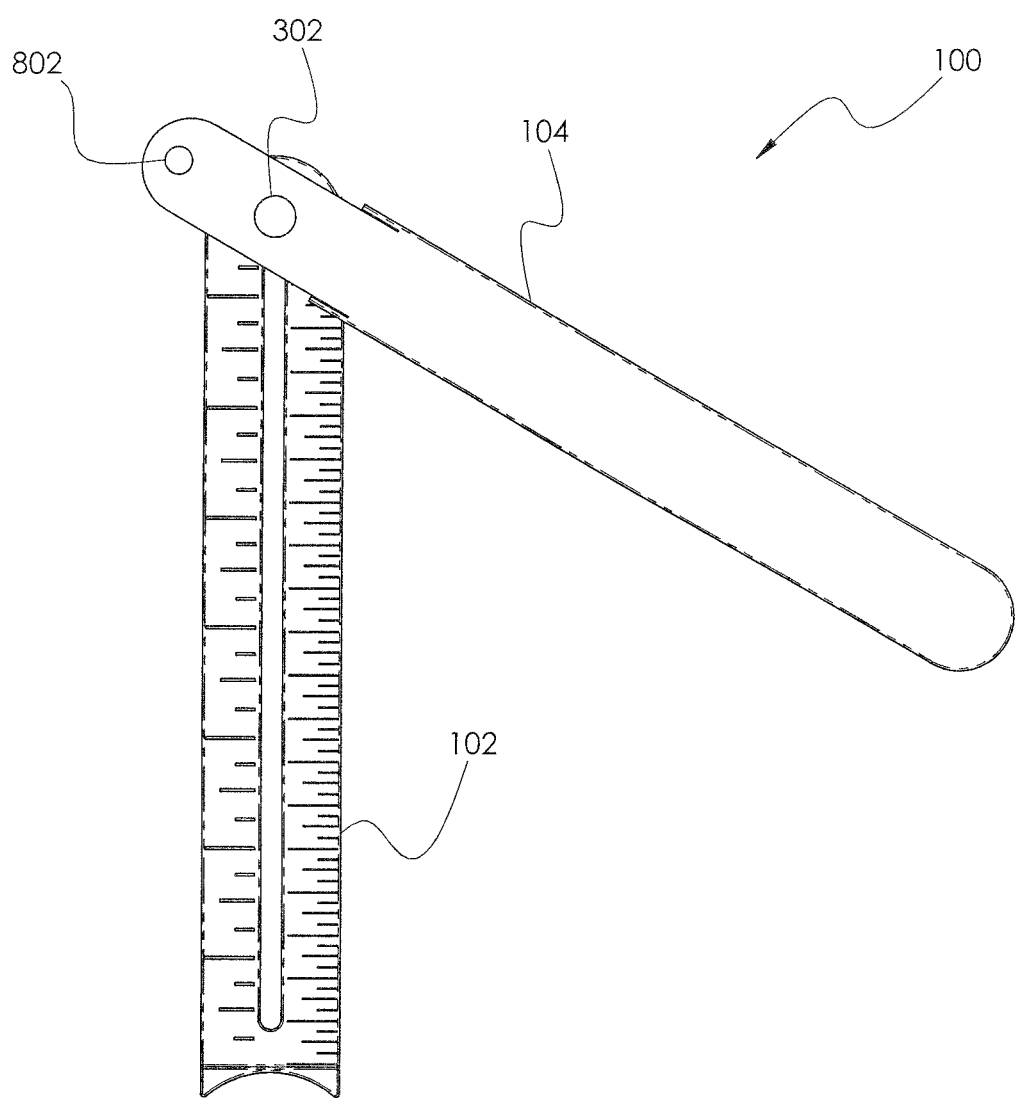
FIG. 8 shows an anterior view of the knee goniometer device in its pivoted state according to an exemplary embodiment.

FIG. 8 shows an anterior view of the knee goniometer device 100 in its pivoted state. The fastener 302 connects the elongated ruler member 102 to the elongated movable member 104. The elongated movable member 104 may pivot to the left side or the right side of the elongated ruler member 102. The elongated movable member 104 pivots down and to the side by the fastener 302 to the elongated ruler member 102. The elongated movable member 104 has a total 180 degree range of motion and ninety degree range of motion on either side of the elongated ruler member 102. For example, FIG. 5 shows the knee goniometer device 100 in the fully deployed state meaning the heel height difference is more than can be measured. The fastener 302 stops the elongated moveable member 104 from moving past this fully deployed position. The elongated movable member 104 has a hanger hole 802 to allow hanging of the knee goniometer device 100 for storage.

Figure 9:
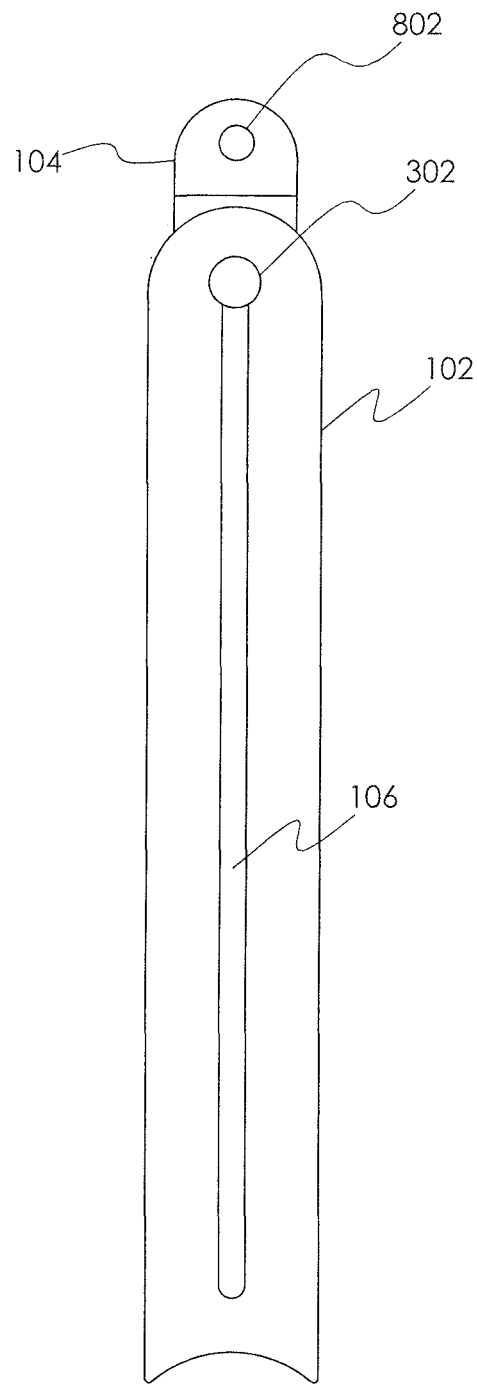
FIG. 9 and FIG. 10 show the posterior view and anterior view, respectfully, of the knee goniometer device in its closed state according to an exemplary embodiment.

FIG. 9 shows a posterior view of the exemplary knee goniometer device 100 in a closed state. The elongated movable member 104 is apparent through the longitudinal slot 106 of the elongated ruler member 102.

Figure 10:
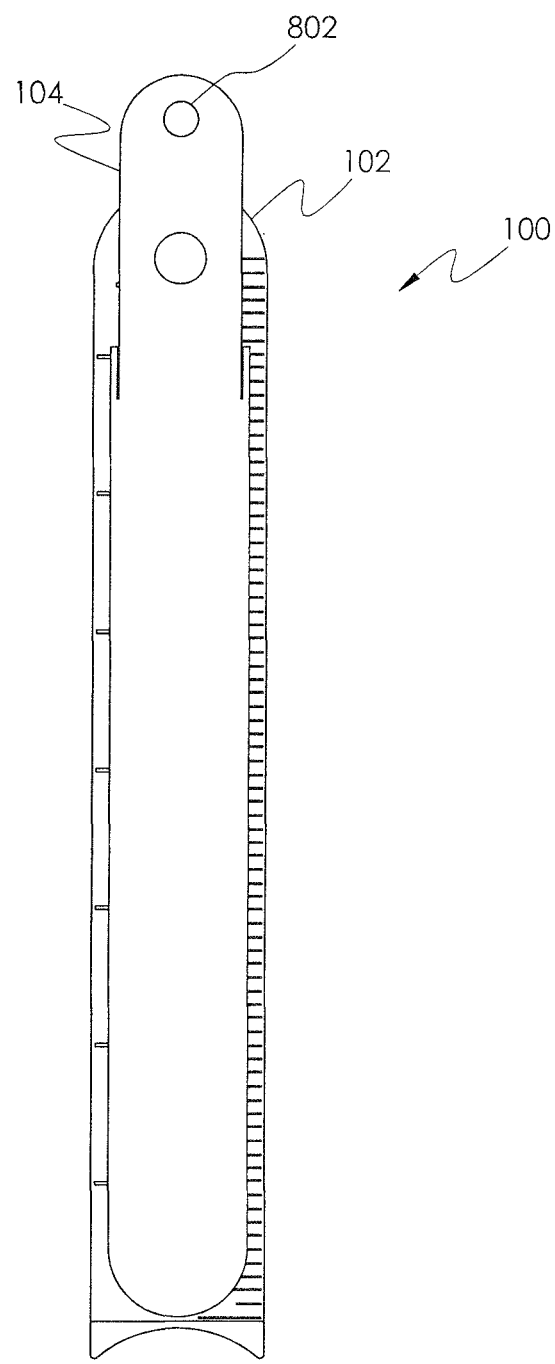

FIG. 10 shows an anterior view of the knee goniometer device 100 in a closed state to allow hanging in a vertical position by hanger hole 802. The elongated movable member 104 rests anterior to the elongated ruler member 102.

Figure 11:
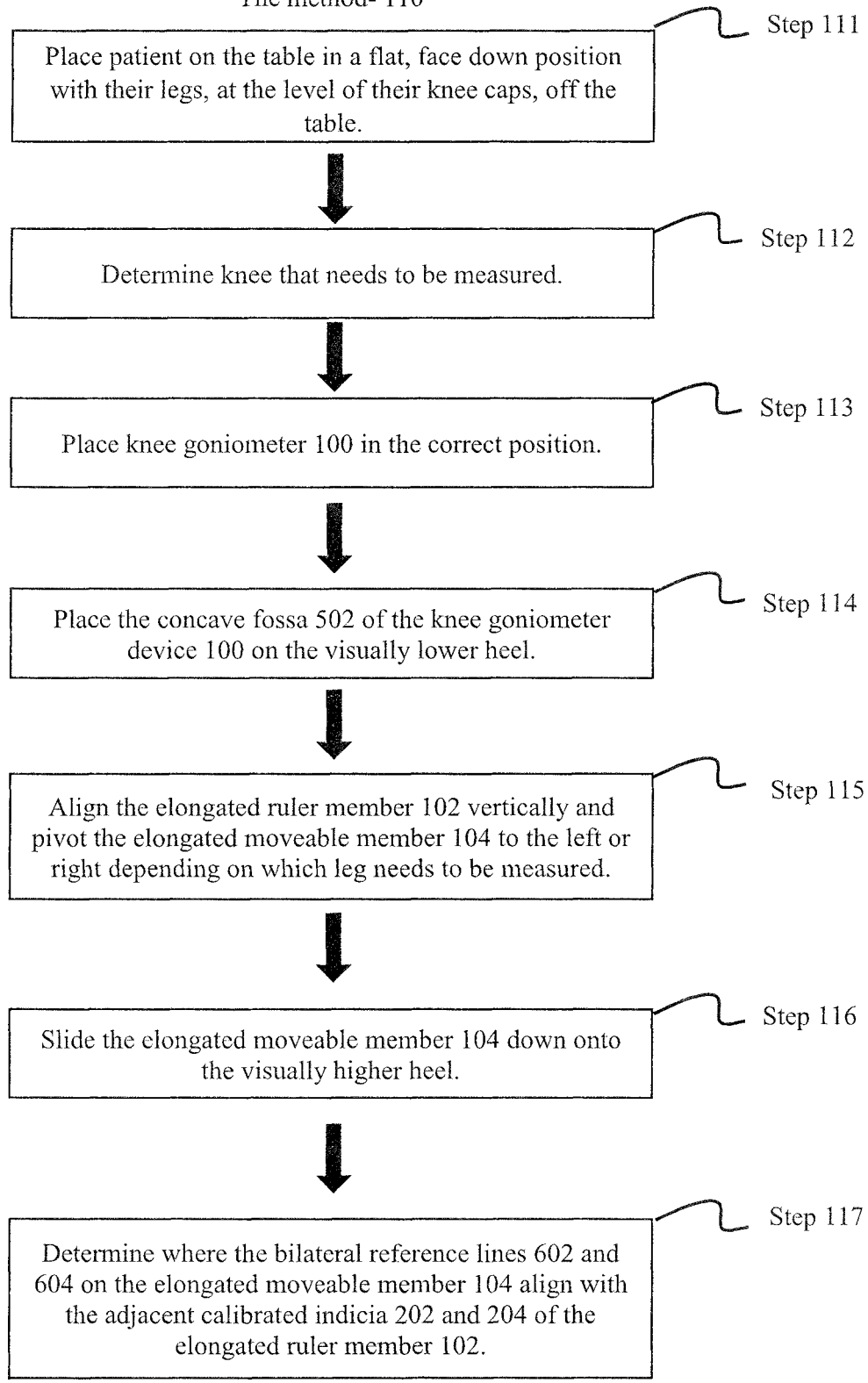
FIG. 11 shows a method of using the knee goniometer device to measure extension loss and hyperextension in a patient's knee joint, by assessing heel height difference while a patient is lying prone on a table with their legs, at the level of their kneecaps, off the table according to an exemplary embodiment.

FIG. 11 shows an exemplary method 110 which is used to measure a patient's affected knee joint using the knee goniometer device 100. In step 111, patient is placed on the table in a flat, face down position with their legs, at the level of their knee caps, off the table. In step 112, the user would determine which knee is affected and needs to be measured. In step 113, the knee goniometer device 100 is placed in the correct position to measure the affected knee. In step 114, the concave fossa 502 of the knee goniometer device 100 is placed on the visually lower heel of the leg. In step 115, the elongated ruler member 102 is vertically aligned and the elongated moveable member 104 is pivoted to the left or right depending on which leg needs to be measured. In step 116, the user slides the elongated moveable member 104 down onto the leg with the visually higher heel. Lastly, in step 117, the user would determine where the bilateral reference lines 602 and 604 on the elongated moveable member 104 align with the adjacent calibrated indicia 202 and 204 of the elongated ruler member 102. The method 110 is a more accurate way of measuring the degree of knee straightness, extension loss, or hyperextension associated with arthritis, trauma surgery or other medical conditions. The method 110 provides an accurate distance measurement that correlates to knee straightness.

Figure 12:
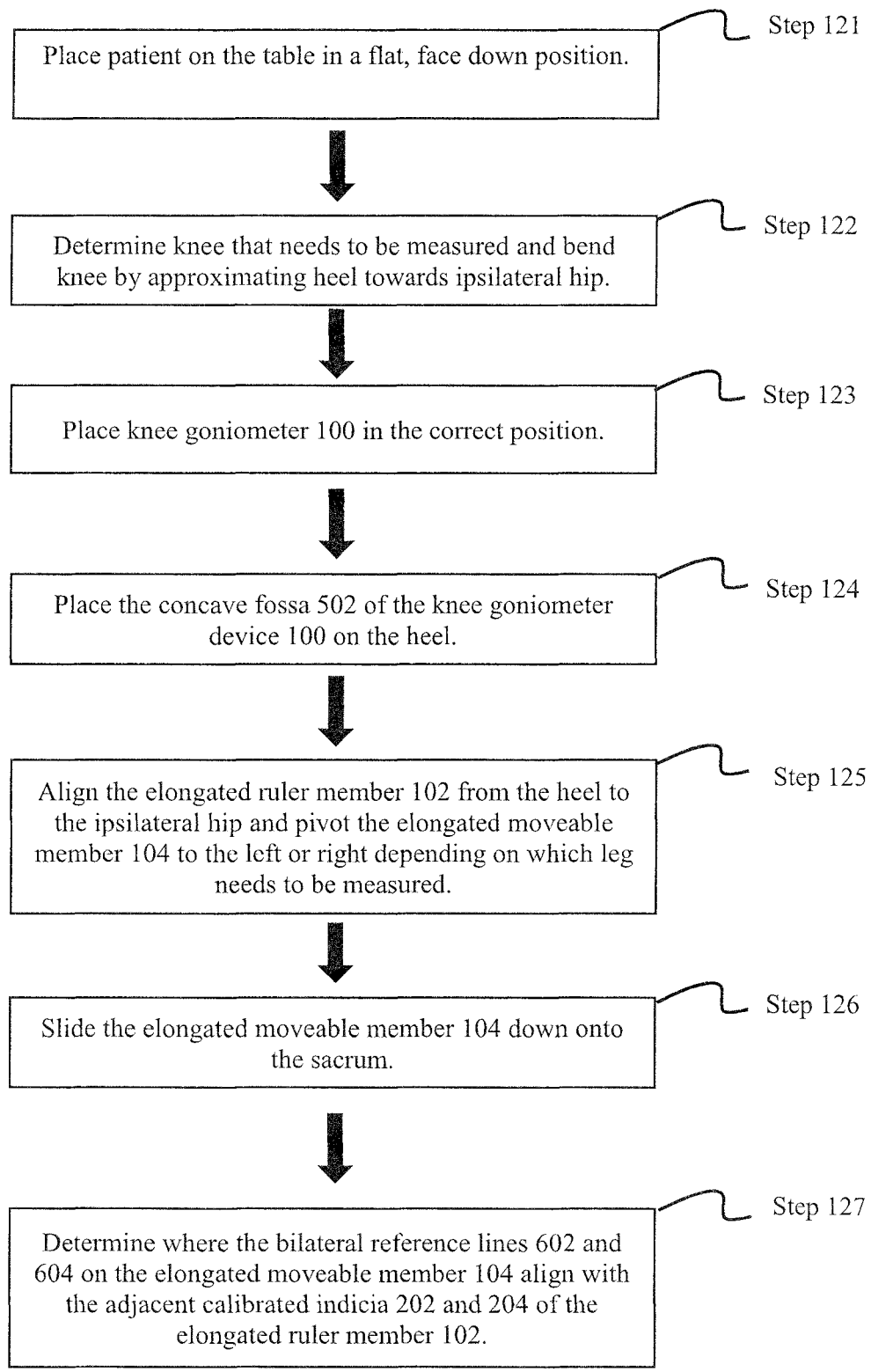
FIG. 12 shows a method of using the knee goniometer device to measure flexibility in the knee extensor length by assessing the distance between the heel and the sacrum while the patent is lying face down on the table with a prone knee bend.

FIG. 12 shows another exemplary method 120 which is used to measure the flexibility of an affected and unaffected knee extensor length. In step 121, the patient is placed on the table in a flat, face down position. In step 122 the user determines the knee that needs to be measured and bends the knee by approximating heel towards ipsilateral hip. In step 123, the knee goniometer 100 is placed in the correct position. In Step 124, the user places the concave fossa 502 on the heel of the leg being measured. In Step 125, the use aligns the elongated ruler member 102 from the heel to the ipsilateral hip and pivots the elongated moveable member 104 to the left or right depending on which legs need to be measured. In Step 126, the user slides the elongated moveable member 104 down onto the sacrum. In step 127, the user determines where the bilateral reference lines 602 and 604 on the elongated moveable member 104 align with the adjacent calibrated indicia 202 and 204 of the elongated ruler member 102.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalent.

What is claimed is:

1. A device, comprising:
    an elongated ruler member having at one end a concave fossa to receive a heel and calibrated indicia disposed on the elongated ruler member; and
    an elongated movable member moveably coupled to the elongated ruler member;
    wherein the elongated movable member provides a reference on the indicia of the elongated ruler member to measure a heel height difference of a patient, and
    wherein the elongated movable member includes a notch that narrows the width of a pivot end of the elongated movable member.

2. The device of claim 1, wherein the elongated movable member and the elongated ruler member are made of a rigid or a semi-rigid material.

3. The device of claim 1, wherein the elongated movable member, at a location proximate to the end of the movable member, has a flange to engage the elongated ruler member in a perpendicular manner.

4. The device of claim 3, wherein the flange has a width equal to the width of the elongated ruler member.

5. The device of claim 1, wherein the elongated ruler member has an abutment with a perpendicular planar surface on the topside of the abutment creating a shelf, wherein the elongated movable member rests on the shelf indicating a measurement of zero.

6. The device of claim 1, wherein the notch is two notches.

7. The device of claim 6, wherein the elongated movable member has a bilateral reference line disposed into a corner of each of the two notches allowing the user to read the adjacent calibrated indicia of the elongated ruler member.

8. The device of claim 1, wherein the elongated movable member flange has one hanger hole.

9. The device of claim 1, wherein the elongated movable member has one through-hole.

10. The device of claim 1, wherein the elongated ruler member further includes a pre-determined central longitudinal slot extending substantially a length of the elongated ruler member.

11. The device of claim 10, wherein the calibrated indicia are disposed adjacent to a path of the longitudinal slot along two edges of the elongated ruler member.

12. The device of claim 1, further comprising:
    a fastener to attach the elongated ruler member and the elongated movable member such that the elongated movable member engages and slides along a length of a longitudinal slot of the elongated ruler member.

13. The device of claim 12, wherein the fastener allows the movable member to pivot in relation to the elongated ruler member.

14. A method of measuring, using the device of claim 1, straightness, extension loss, or hyperextension in a patient's knee joint, by assessing heel height difference while patient is lying prone on a table with their legs, at the level of their knee caps, off the table, comprising:
    a. placing the concave fossa on the visually lower posterior heel of the patient's leg while patient is lying prone, face down, on a table with their legs, at the level of their knee caps, off the table,
    b. aligning the elongated ruler member vertically, and pivoting the elongated movable member to the left or right such that the elongated movable member is substantially perpendicular to the elongated ruler member,
    c. sliding the elongated movable member downward onto a visually higher posterior heel of patient's leg wherein the reference lines on the elongated movable member align with the adjacent calibrated indicia of the elongated ruler member.

15. A method of measuring, using the device of claim 1, flexibility of an affected and unaffected knee extensor length by measuring the distance between the heel and the sacrum while patient is placed in a flat, face down position on the table comprising:
- a. bending the knee and approximating the heel towards ipsilateral hip, placing the device in the correct position and the concave fossa on the heel of the leg being measured,
- b. aligning the elongated ruler member from the heel to the ipsilateral hip and pivoting the elongated moveable member to the left or right depending on which legs need to be measured, sliding the elongated moveable member down onto the sacrum,
- c. determining where the bilateral reference lines on the elongated moveable member align with the adjacent calibrated indicia of the elongated ruler member.

\* \* \* \* \*